(12) United States Patent
Butcher et al.

(10) Patent No.: US 9,891,162 B2
(45) Date of Patent: Feb. 13, 2018

(54) PHOTOMETRIC MEASUREMENT CELL

(71) Applicant: Rosemount Analytical Inc., Irvine, CA (US)

(72) Inventors: Bradley A. Butcher, La Verne, CA (US); Chang-Dong Feng, Long Beach, CA (US); Jeffrey Lomibao, Corona, CA (US); Calin Ciobanu, Brea, CA (US)

(73) Assignee: Rosemount Analytical Inc., Irvine, CA (US)

( * ) Notice: Subject to any disclaimer, the term of this patent is extended or adjusted under 35 U.S.C. 154(b) by 281 days.

(21) Appl. No.: 14/502,454

(22) Filed: Sep. 30, 2014

(65) Prior Publication Data
US 2015/0099304 A1   Apr. 9, 2015

Related U.S. Application Data (60) Provisional application No. 61/886,293, filed on Oct. 3, 2013.

(51) Int. Cl.
*G01N 33/18* (2006.01)
*G01N 21/27* (2006.01)
(Continued)

(52) U.S. Cl.
CPC ............ *G01N 21/01* (2013.01); *G01N 21/11* (2013.01); *G01N 21/251* (2013.01); *G01N 21/27* (2013.01);
(Continued)

(58) Field of Classification Search
CPC ................ G01N 21/251; G01N 21/01
See application file for complete search history.

(56) References Cited

U.S. PATENT DOCUMENTS 3,874,850 A * 4/1975 Sorensen .......... G01N 33/4925
                                                      204/412
5,550,053 A    8/1996 Salpeter
(Continued)

FOREIGN PATENT DOCUMENTS

EP        1482298 A1    12/2004

OTHER PUBLICATIONS

First Office Action for Chinese Patent Application No. 201480004538.8 dated Oct. 8, 2016, 13 pages.
(Continued)

*Primary Examiner* — Krishnan S Menon
*Assistant Examiner* — Dwan A Gerido
(74) *Attorney, Agent, or Firm* — Christopher R. Christenson; Kelly, Holt & Christenson PLLC (57) ABSTRACT

An online colorimetric analyzer that generates an indication of a material in a sample is provided. The analyzer includes a peristaltic pump configured to convey. A photometric cell is operably coupled to the peristaltic pump to receive the sample. An illumination source is disposed to direct illumination through the sample in the photometric cell along an angle of incidence. A photodetector disposed to receive illumination passing through the photometric cell along the angle of incidence and provide a signal indicative of a color of the sample. A controller is coupled to the illumination source, the photodetector and the peristaltic pump. The photometric cell is tilted relative to vertical such that a surface of liquid present when the photometric cell is partially filled substantially reflects the illumination away from the angle of incidence.

8 Claims, 7 Drawing Sheets

(51) Int. Cl.
   *G01N 21/01* (2006.01)
   *G01N 21/25* (2006.01)
   *G01N 21/78* (2006.01)
   *G01N 31/22* (2006.01)
   *G01N 21/11* (2006.01)
   *G01F 23/292* (2006.01)
   *G01N 21/84* (2006.01)

(52) U.S. Cl.
   CPC ............ *G01N 21/78* (2013.01); *G01N 31/22* (2013.01); *G01F 23/292* (2013.01); *G01N 2021/8416* (2013.01)

(56) References Cited

U.S. PATENT DOCUMENTS

| | | | |
|---|---|---|---|
| 7,333,194 | B2 | 2/2008 | Jaunakais et al. |
| 2010/0196945 | A1* | 8/2010 | Forsell ............... G01N 15/05 435/29 |
| 2011/0318767 | A1 | 12/2011 | Takagi et al. |
| 2015/0233838 | A1 | 8/2015 | Butcher et al. |

OTHER PUBLICATIONS

First Examination Report for Australian Patent Application No. 2014329519 dated Nov. 25, 2016, 4 pages.
EPO Communication for European Patent Application No. 14850275.0, dated Feb. 20, 2017, 9 pages.
Office Action for Canadian Patent Application No. 2,926,204 dated Dec. 19, 2016, 3 pages.
Second Office Action for Chinese Patent Application No. 201480004538.6, dated Jun. 14, 2017, 8 pages including translation.
Second Examination for Australian Patent Application No. 2014329519, dated Jul. 7, 2017, 3 pages.
International Search Report and Written Opinion for International Application No. PCT/US2014/058785, dated Jan. 9, 2015, date of filing: Oct. 2, 2014, 11 pages.
International Search Report and Written Opinion for International Application No. PCT/US2015/016556, dated May 22, 2015, date of filing: Feb. 19, 2015, 12 pages.
Office Action for Canadian Patent Application No. 2,926,204, dated Oct. 3, 2017; 3 pages.

* cited by examiner

PHOTOMETRIC MEASUREMENT CELL

CROSS-REFERENCE TO RELATED APPLICATION

The present application is based on and claims the benefit of U.S. Provisional Patent Application Ser. No. 61/886,293, filed Oct. 3, 2013, the content of which is hereby incorporated by reference in its entirety.

BACKGROUND

Online wet chemistry analyzers are used in a variety of industries to provide a continuous indication of an analyte in a process sample. This continuous indication can be provided locally by the analyzer and/or remotely to one or more suitable devices in order to provide control and/or monitoring of a chemical process.

One particular type of online wet chemistry analyzer is an online silica analyzer. These devices are configured to generate a reaction in the process sample that allows an indication of silica in the sample to be determined. Such analyzers are useful in determining silica content in boiler water, boiler feedwater, demineralized water, and steam condensate. While such analyzers are useful in a variety of industries, they are of particular use in power plant boilers. In such systems, silica can form silicate deposits that can damage turbines and other generation equipment that is used in the water-steam turbine cycle. Accordingly, power plants with high pressure turbines generally monitor silica carefully in order to ensure effective detection and removal/remediation. One particular example of an online silica analyzer is sold under the trade designation Model CFA3030 Silica Analyzer from Rosemount Analytical, an Emerson Process Management company.

An online silica analyzer will generally employ a known reaction to render the silica in the process sample readily detectable. One example of such a reaction is known as the molybdenum blue method. In the molybdenum blue method, molybdate (usually in the form of potassium molybdate) is used to react with silica in the process sample/solution in order to generate a compound suitable for colorimetric detection. In accordance with the molybdenum blue method, the silica content in water is measured based on the color of the silicomolybdic acid formed through the wet chemistry process.

SUMMARY

An online colorimetric analyzer that generates an indication of a material in a sample is provided. The analyzer includes a peristaltic pump configured to convey. A photometric cell is operably coupled to the peristaltic pump to receive the sample. An illumination source is disposed to direct illumination through the sample in the photometric cell along an angle of incidence. A photodetector disposed to receive illumination passing through the photometric cell along the angle of incidence and provide a signal indicative of a color of the sample. A controller is coupled to the illumination source, the photodetector and the peristaltic pump. The photometric cell is tilted relative to vertical such that a surface of liquid present when the photometric cell is partially filled substantially reflects the illumination away from the angle of incidence.

DETAILED DESCRIPTION OF ILLUSTRATIVE EMBODIMENTS

A variety of colorimetric wet chemistry analyzers employ peristaltic pumps in order to convey sample mixtures to and from a measurement cell. Peristaltic pumps utilize deformable tubing and a drive that generally deforms the tubing to move the sample along. Peristaltic pumps are used in wet chemistry analyzers to deliver sample solution as well as one or more reagents. However, the tubing itself will age with usage and the volume of liquid conveyed per turn will accordingly decrease with aging. In order to control the delivery volume, an automatic wet chemistry analyzer currently relies on the number of turns of a digital motor which drives the peristaltic pump. During the operation of the wet chemistry analyzer, it is important to calibrate the pump delivery speed (volume/time unit) such that decreases in peristaltic pump activity as the tubing ages can be detected and compensated.

Figure 1:
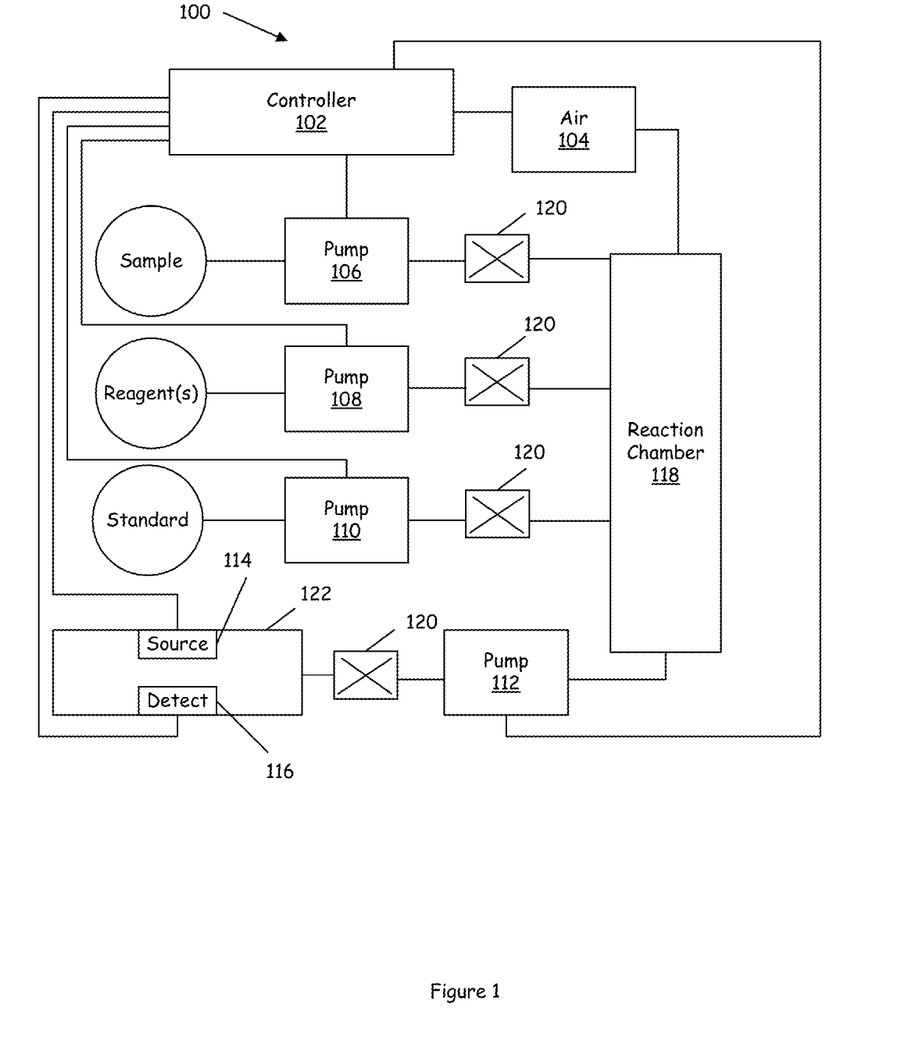
FIG. 1 is a diagrammatic view of an online silica analyzer with which embodiments of the present invention are particularly useful.

FIG. 1 is a diagrammatic view of an online silica analyzer with which embodiments of the present invention are particularly useful. Analyzer 100 includes controller 102 that is coupled to air source 104, pumps 106, 108, 110, and 112. Additionally, controller 102 is also coupled to illumination source 114 and illumination detector 116. Typically, each pump 106, 108, 110, and 112 is a peristaltic pump that employs peristaltic action to move its respective liquid. Cavity volumes are typically 5 mL for sample and standards (pumps 106 and 110) and 0.2 mL for reagents (pump 108). A vacuum/pressure pump (not shown) pushes and pulls on the membrane. Vacuum causes the chamber to fill. Pressure pushes the liquid out of the cavity into reaction chamber 118. A number of check valves 120 are provided in order to prevent backflow. When mixing of the sample/reagent/standards is desired, controller 102 engages air source 104 to pump a quantity of air into reaction chamber 118 in order to mix the contents therein. After a suitable reaction time has passed, the treated sample is pumped, using pump 112, to measurement cell 122. Once the mixed sample is provided within measurement cell 122, controller 102 engages illumination source 114 to direct light through the mixed sample toward detector 116. In accordance with known techniques, the illumination detected by detector 116 provides an indication of the analyte (silica) in the sample. Controller 102 automatically calculates the absorbance and translates the results into a silica concentration reading. Once the measurement is complete, repeated flushes with fresh sample remove the treated sample from the measurement and reaction cells, 122 and 118, respectively.

Figure 2:
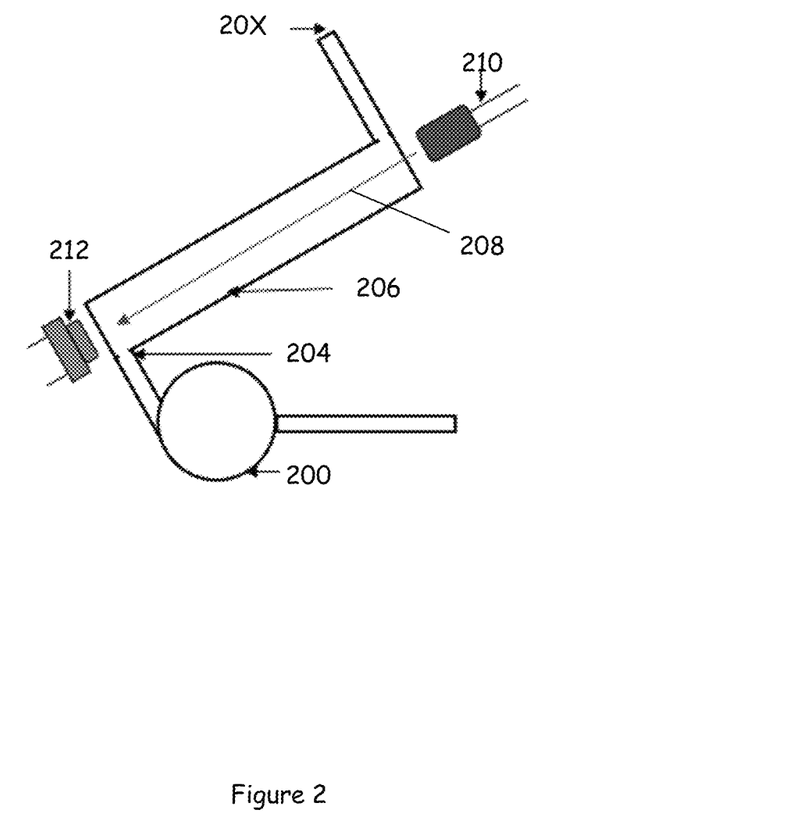
FIG. 2 is a diagrammatic view of a photometric cell used in online analyzers in accordance with an embodiment of the present invention.

In accordance with an embodiment of the present invention, a tilted photometric cell 206 is provided as well as a method to measure the volume of liquid delivered to the cell from a peristaltic pump. As shown in FIG. 2, peristaltic pump 200 has an inlet 202 that receives a sample mixture. When photometric cell 206 is empty, illumination 208 travels along an angle of incidence and reaches photodetector 212. With no sample mixture in photometric cell 206, substantially all illumination 208 will reach detector 212.

Figure 3A:
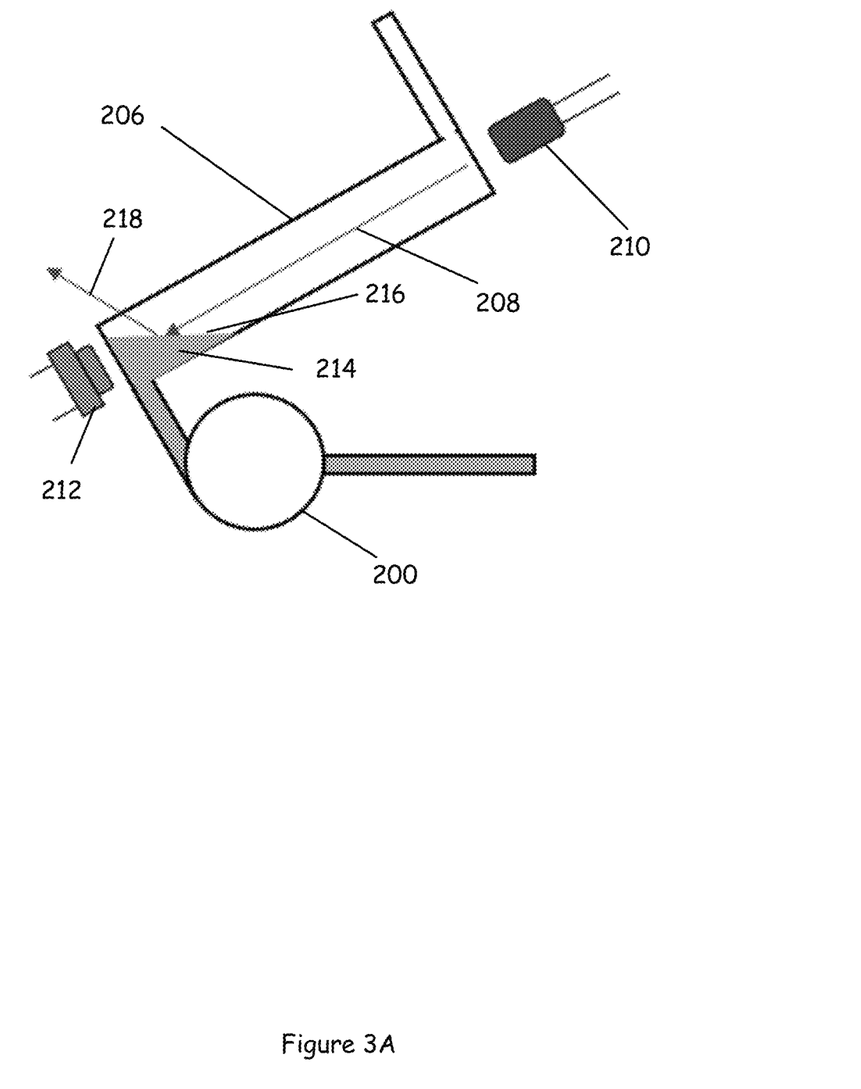
FIG. 3A is a diagrammatic view of a photometric cell filling with liquid in accordance with an embodiment of the present invention.
Figure 3B:
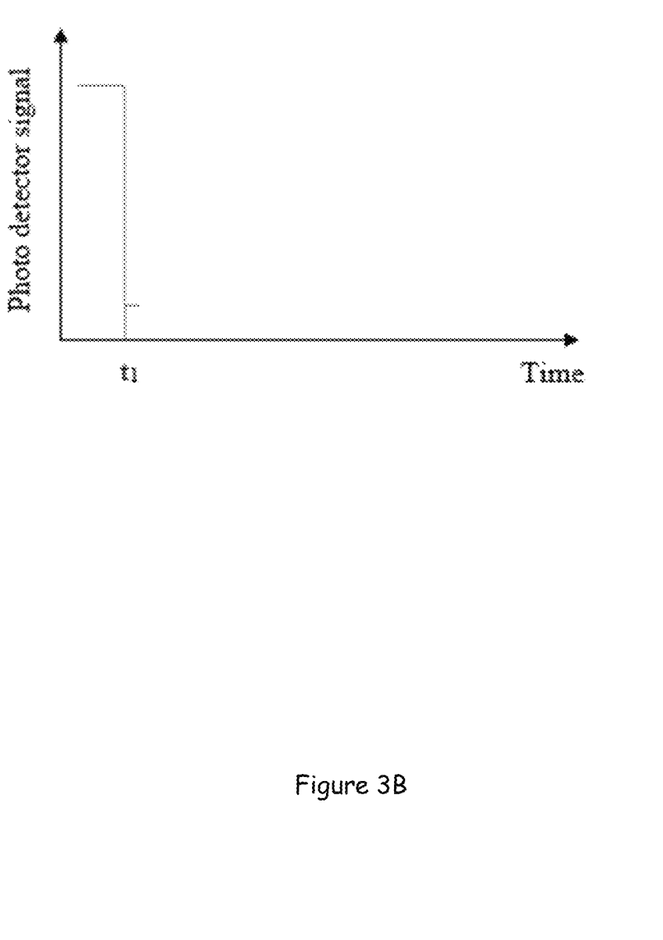
FIG. 3B is a chart illustrating photodetector response over time for the photometric cell shown in FIG. 3A.

The sample mixture is conveyed by peristaltic pump 200 through outlet 204 to photometric cell 206. As the mixture slowly fills photometric cell 206, the angle of the surface of the liquid will reflect a substantial portion of illumination 208 from light source 210 away from detector 212 until the entire photometric cell 206 is substantially filled with the mixture. At such time, the reflection of the substantial portion of illumination 208 will no longer occur, and a significant portion of illumination 208 will then reach photo detector 212. As shown in FIG. 2, photometric cell 206 is disposed at an angle relative to vertical such that the surface 216 (shown in FIG. 3A) of liquid present when the photometric cell is partially filled reflects the illumination away from the angle of incidence FIG. 3A illustrates peristaltic pump 200 beginning to pump liquid 214 into photometric cell 206. As can be seen, illumination 208 from source 210 impinges surface 216 of liquid 214 and is reflected as beam 218. Accordingly, the vast majority of the illumination in beam 218 does not reach detector 212. FIG. 3B shows a diagrammatic chart of the photo detector response signal as a function of time. When the sample liquid enters the bottom of photometric cell 206, most of illumination 208 gets reflected by surface 216 of liquid 214 due to the tilt of photometric cell 216. This causes a readily measurable drop in the signal output from detector 212. This drop can be seen at time $T_1$ in FIG. 3B.

Figure 4A:
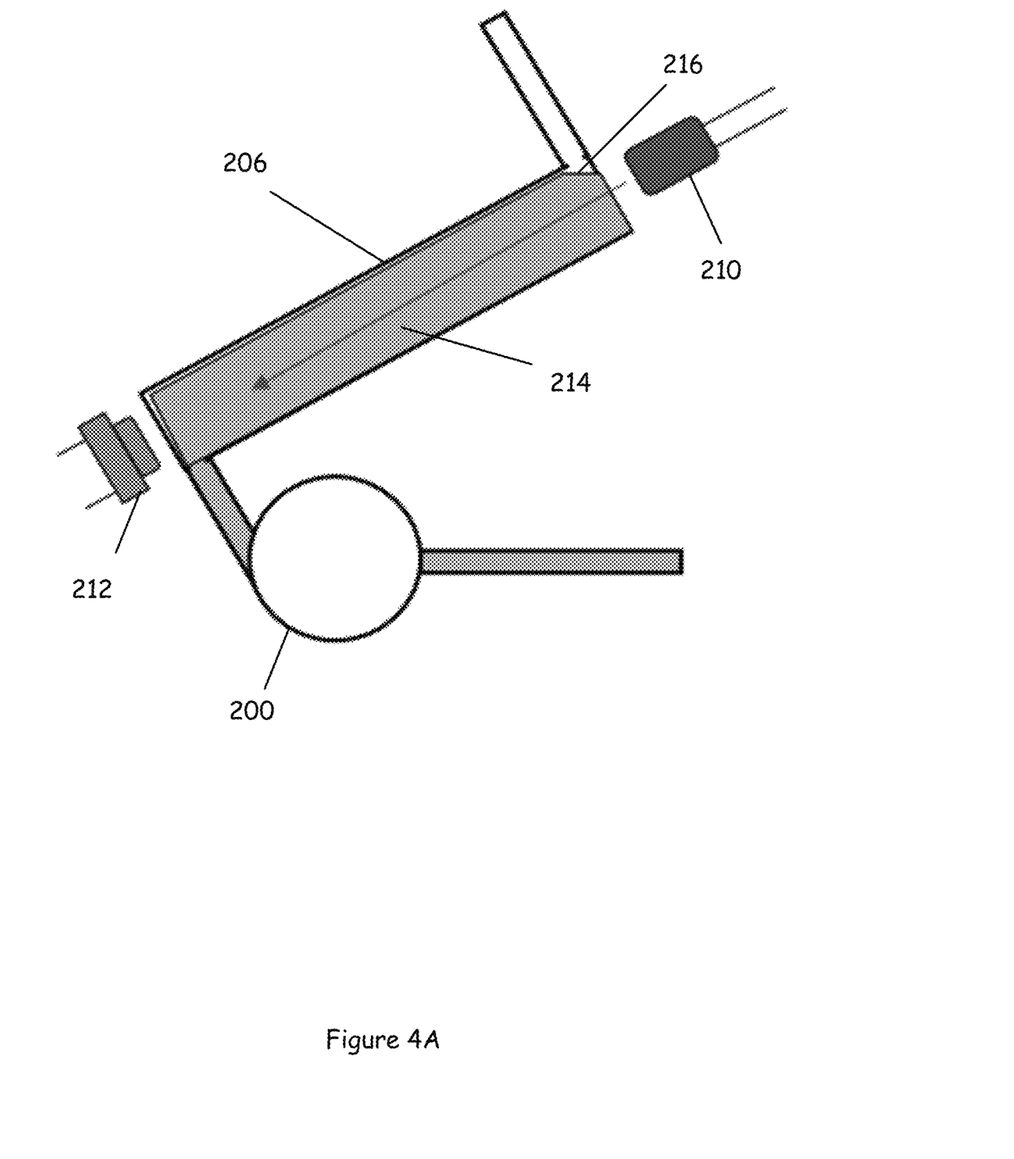
FIG. 4A is a diagrammatic view of a photometric cell filled with liquid in accordance with an embodiment of the present invention.
Figure 4B:
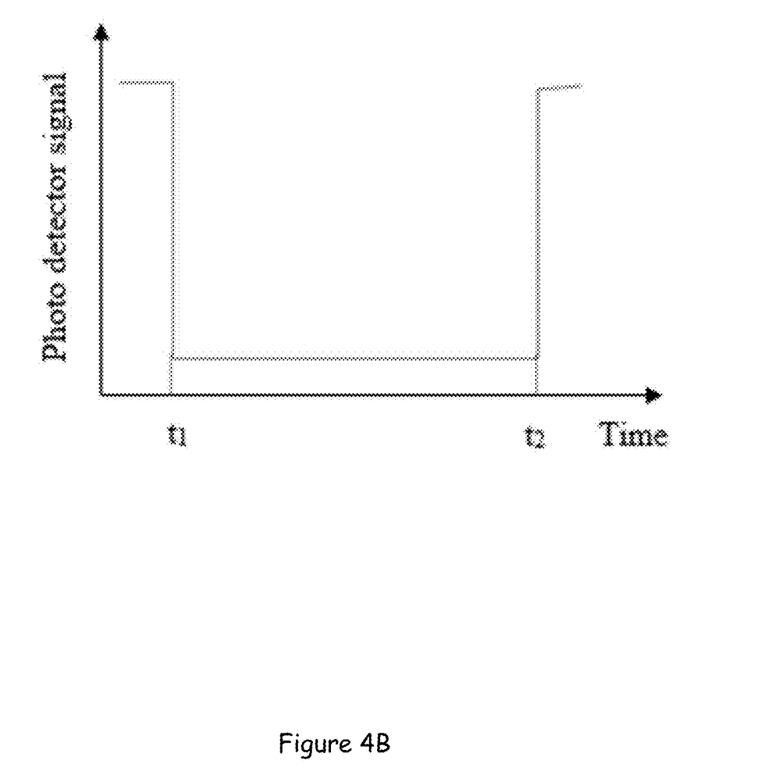
FIG. 4B is a chart illustrating photodetector response over time for the photometric cell shown in FIG. 4A.

FIG. 4A is a diagrammatic view of photometric cell being substantially filled with liquid 214. As shown in FIG. 4A, surface 216 is now above the entry point of illumination beam 208 into photometric cell 206. Accordingly, surface 216 does not reflect illumination 208 away from detector 212. As a result, once surface 216 surpasses the entry point of illumination 208 into photometric cell 206, photo detector 212 will receive full light from light source 210. This marked increase in the photo detector signal is shown in FIG. 4B. Accordingly, when photometric cell 206 is completely empty, detector 212 will receive the full light from light source 210. However, when there is enough sample liquid to cover the bottom of photometric cell 206 (shown in FIG. 3A) the light will be reflected mostly, and the photo detector will only receive a small amount of light, thereby causing a sudden drop in the output signal of detector 212. This situation continues as the liquid level rises, until liquid level 216 reaches the top of photometric cell 206, as shown in FIG. 4A. When this occurs, it results in a sudden rise in the photo detector signal, as shown at time $t_2$ in FIG. 4B.

At a constant pump delivery speed, R, if the controller of the analyzer is tracking or otherwise monitoring the signal of photo detector 212 over time, $t_1$ will be detected when the signal drops, and $t_2$ will be detected when the signal rises again. Since the liquid volume difference in the cell 206 between FIGS. 3A and 4A is a fixed volume, V, the pump delivery speed can then be calculated as:

$$R = V/(t_2 - t_1).$$

This pump delivery speed can be used to adjust analyzer operation and thereby compensate for the aging of the flexible tubing in the peristaltic pump. Additionally, the calculated pump delivery speed R can be compared with an initial pump delivery speed that is measured or otherwise determined when the wet chemistry analyzer is new such that wear or deterioration of the peristaltic pump over time can be characterized. This allows the pump to be repaired or replaced as appropriate, before a significant effect on analyzer operation occurs.

While the embodiment described above calculates pump delivery speed based on filling photometric cell 206, embodiments of the present invention also include reversing peristaltic pump 200 and detecting changes in signals indicative of the liquid emptying from photometric cell 206. Further, the pump delivery speed calculated based on filling photometric cell 206 can be combined with the pump delivery speed calculated based on emptying photometric cell 206 in any suitable manner, such as by averaging the two values.

Figure 5:
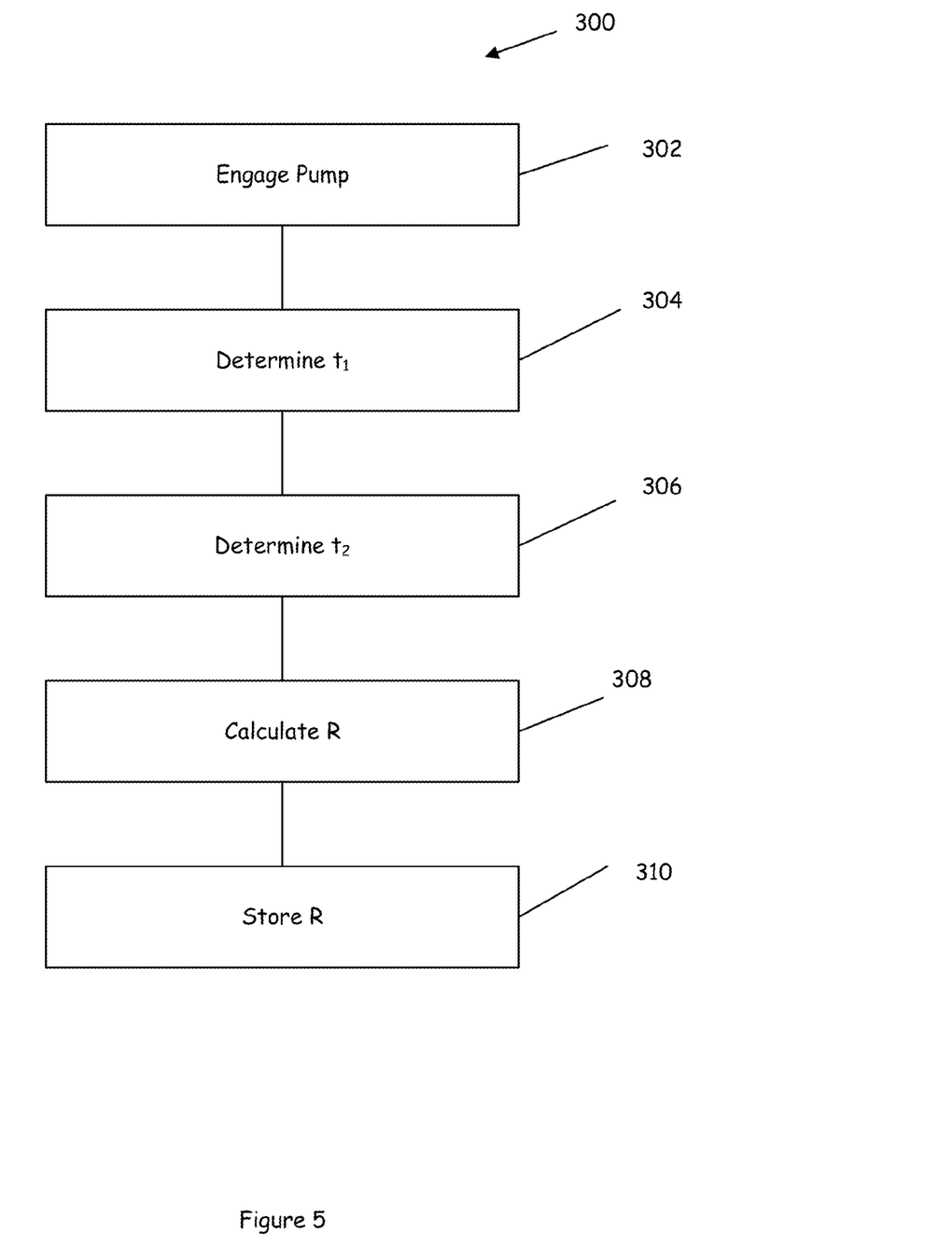
FIG. 5 is a flow diagram of a method 300 of measuring peristaltic pump delivery speed in a wet chemistry analyzer in accordance with an embodiment of the present invention.

FIG. 5 is a flow diagram of a method 300 of measuring peristaltic pump delivery speed in a wet chemistry analyzer in accordance with an embodiment of the present invention. Method 300 begins at block 302 where a peristaltic pump of the wet chemistry analyzer is engaged to begin filling a tilted photometric cell. Next, at block 304, the output of a detector of the photometric cell is monitored to determine a time when the photo detector signal drops. This time is stored as time $t_1$. Next, at block 306, the peristaltic pump continues filling the photometric cell until the detector signal rises again. When the detector signal rises again (such as shown in FIG. 4B) time $t_2$ is obtained and stored. Next, at block 308, a processor of the wet chemistry analyzer determines pump delivery speed based on a known fixed volume of the photometric cell and the difference between times $t_1$ and $t_2$. This calculated pump delivery speed is then stored at block 310 such that changes in the flexibility of the tubing of the peristaltic pump, such as occurs with age, can be determined and compensated. The calculated pump delivery speed can thus be used for subsequent analyses. Additionally, the measurement of the filling duration and subsequent pump speed calculation can be performed at regular intervals and/or in response to technician input, such as through a user interface of the analyzer.

Although the present invention has been described with reference to preferred embodiments, workers skilled in the art will recognize that changes may be made in form and detail without departing from the spirit and scope of the invention.

What is claimed is:

1. An online colorimetric analyzer for providing an indication of a material in a sample, the analyzer comprising:
   a peristaltic pump that conveys the sample;
   a photometric cell operably coupled to the peristaltic pump to receive the sample;
   an illumination source disposed to direct illumination through the sample in the photometric cell along an angle of incidence;
   a photodetector disposed to receive illumination passing through the photometric cell along the angle of incidence and provide a first signal indicative of a color of the sample, at a first time, and a second signal indicative of the color of the sample, wherein the second signal is at a second time, wherein the second time is later than the first time;
   a controller coupled to the illumination source, the photodetector and the peristaltic pump; and
   wherein the photometric cell is tilted relative to vertical such that a surface of liquid present when the photometric cell is partially filled reflects a detectable portion of the illumination away from the angle of incidence, and wherein the controller detects a change between the first and second signals, wherein the change is indicative of the photometric cell being filled.

2. The online colorimetric analyzer of claim 1, wherein the controller monitors a photodetector response while the peristaltic pump is filling the photometric cell and relates a duration of relatively low photodetector signal to a control signal provided to the peristaltic pump.

3. The online colorimetric analyzer of claim 2, wherein the controller calculates pump delivery speed based on the measured time.

4. The online colorimetric analyzer of claim 3, wherein the controller stores the calculated pump delivery speed.

5. The online colorimetric analyzer of claim 3, wherein the uses the stored pump delivery speed for a subsequent analysis cycle.

6. The online colorimetric analyzer of claim 5, wherein the analyzer is a silica analyzer.

7. The online colorimetric analyzer of claim 6, and further comprising a reaction chamber coupled to the peristaltic pump to provide the sample after a reaction.

8. The online colorimetric analyzer of claim 1, wherein the controller monitors the photodetector response while the peristaltic pump is emptying the photometric cell.

* * * * *

UNITED STATES PATENT AND TRADEMARK OFFICE
CERTIFICATE OF CORRECTION

PATENT NO. : 9,891,162 B2
APPLICATION NO. : 14/502454
DATED : February 13, 2018
INVENTOR(S) : Bradley A. Butcher et al.

Page 1 of 1

It is certified that error appears in the above-identified patent and that said Letters Patent is hereby corrected as shown below:

On the Title Page

Abstract: Line 3: insert --the sample-- after the word "convey"

In the Claims

Column 5, Claim 5: Line 16: insert --controller-- after the word "the"

Signed and Sealed this
Nineteenth Day of June, 2018

Andrei Iancu
*Director of the United States Patent and Trademark Office*